(12) United States Patent  
Lim

(10) Patent No.: US 12,134,345 B2  
(45) Date of Patent: Nov. 5, 2024

(54) VEHICLE

(71) Applicants: Hyundai Motor Company, Seoul (KR); Kia Corporation, Seoul (KR)

(72) Inventor: Kyu Hyung Lim, Gwacheon-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 128 days.

(21) Appl. No.: 17/958,919

(22) Filed: Oct. 3, 2022

(65) Prior Publication Data

US 2023/0150423 A1 May 18, 2023

(30) Foreign Application Priority Data

Nov. 18, 2021 (KR) .................. 10-2021-0159603

(51) Int. Cl.
| | |
|---|---|
| *B60Q 1/00* | (2006.01) |
| *A61B 5/00* | (2006.01) |
| *B60Q 1/46* | (2006.01) |
| *B60R 21/013* | (2006.01) |
| *B60R 22/48* | (2006.01) |
| *E05F 15/72* | (2015.01) |
| *G01C 21/26* | (2006.01) |
| *B60R 21/16* | (2006.01) |

(52) U.S. Cl.
CPC ............. *B60Q 1/46* (2013.01); *A61B 5/4809* (2013.01); *B60R 21/013* (2013.01); *B60R 22/48* (2013.01); *E05F 15/72* (2015.01); *G01C 21/26* (2013.01); *A61B 2503/22* (2013.01); *B60R 21/16* (2013.01); *B60R 2022/4816* (2013.01); *B60R 2022/4866* (2013.01); *E05Y 2400/52* (2013.01); *E05Y 2800/252* (2013.01); *E05Y 2900/531* (2013.01); *E05Y 2900/55* (2013.01)

(58) Field of Classification Search
CPC .......... A61B 2560/0242; A61B 5/1112; A61B 5/6893; A61B 5/746; A61B 5/18; B60W 50/02; B60W 40/02; B60W 40/08; B60W 40/105; B60W 2040/0863; B60W 2050/0005; B60W 2420/403; B60W 2520/10; B60W 2556/45; B60Q 1/52; B60S 1/0807; G08G 1/205

See application file for complete search history.

(56) References Cited

U.S. PATENT DOCUMENTS

| | | | | |
|---|---|---|---|---|
| 6,124,783 | A | * | 9/2000 | Alexander ............ B60R 25/104 340/471 |
| 6,268,793 | B1 | * | 7/2001 | Rossi .................. B60Q 1/5035 340/471 |

(Continued)

*Primary Examiner* — Phutthiwat Wongwian  
*Assistant Examiner* — Sherman D Manley  
(74) *Attorney, Agent, or Firm* — Slater Matsil, LLP

(57) ABSTRACT

An embodiment vehicle includes an emergency light, a plurality of detectors, a communication device, and a processor configured to determine whether the vehicle is in a normal state based on detection information of the plurality of detectors when the emergency light is in a turned-on state, determine a turning-on cause of the emergency light based on current location information received by the communication device when it is determined that the vehicle is in the normal state, and control the communication device to transmit guide information corresponding to the determined turning-on cause of the emergency light to an external device.

20 Claims, 7 Drawing Sheets

(56) References Cited

U.S. PATENT DOCUMENTS

| | | | | |
|---|---|---|---|---|
| 6,304,174 B1* | 10/2001 | Smith | ............... | B60Q 1/5035 |
| | | | | 340/471 |
| 9,884,628 B1* | 2/2018 | Grant | ................ | B60W 40/08 |
| 10,525,979 B1* | 1/2020 | Grant | ................ | B60W 40/08 |
| 11,017,676 B2* | 5/2021 | England | ................ | G08G 1/20 |
| 2003/0016146 A1* | 1/2003 | Bates | ................ | G08G 1/205 |
| | | | | 340/471 |
| 2005/0037730 A1* | 2/2005 | Montague | ............ | B60R 25/102 |
| | | | | 455/456.1 |
| 2009/0002145 A1* | 1/2009 | Berry | ................ | H04W 4/90 |
| | | | | 340/436 |
| 2009/0167564 A1* | 7/2009 | Long-Tai | ........... | B62D 15/0285 |
| | | | | 340/932.2 |
| 2011/0210864 A1* | 9/2011 | Tremonti | ............ | G08G 1/0965 |
| | | | | 340/902 |
| 2011/0281545 A1* | 11/2011 | Murakami | ........... | G08B 25/016 |
| | | | | 455/404.1 |
| 2013/0044008 A1* | 2/2013 | Gafford | ................ | G08G 1/205 |
| | | | | 340/471 |
| 2016/0362080 A1* | 12/2016 | Kim | ................ | B60R 21/0134 |
| 2018/0075744 A1* | 3/2018 | Seo | ................ | G01C 21/3605 |
| 2018/0336786 A1* | 11/2018 | Salter | ................ | B60Q 9/008 |
| 2019/0135214 A1* | 5/2019 | Na | ................ | E05F 15/72 |
| 2022/0126691 A1* | 4/2022 | Yu | ................ | B60K 35/00 |
| 2022/0126871 A1* | 4/2022 | Li | ................ | B60W 60/0017 |
| 2023/0347876 A1* | 11/2023 | Quint | ................ | B60W 30/14 |

* cited by examiner

VEHICLE

CROSS-REFERENCE TO RELATED APPLICATIONS

This application claims the benefit of Korean Patent Application No. 10-2021-0159603, filed on Nov. 18, 2021, which application is hereby incorporated herein by reference.

TECHNICAL FIELD

The disclosure relates to a vehicle.

BACKGROUND

A vehicle, which is a machine that travels on a road by rotating wheels, is equipped with various devices for protecting occupants, assisting driving, and improving riding comfort.

An accident may occur due to a breakdown of the vehicle itself, or may occur due to negligence of a driver of the vehicle, negligence of a driver of another vehicle, or road conditions.

Recently, various technologies have been developed for preventing an accident of a vehicle. As an example, technologies have been developed to install a distance sensor in a vehicle to detect an obstacle around the vehicle and warn a driver of the obstacle. Through this method, accidents may be prevented in advance.

Nevertheless, when a vehicle accident occurs, a rescue request may not be possible depending on a severity level of the accident or a degree of injury of the occupant. Therefore, the rescue operation may be delayed, which may aggravate the injuries of the occupants or threaten their lives.

SUMMARY

The disclosure relates to a vehicle. Particular embodiments relate to a vehicle that transmits rescue information in response to an abnormal state of the vehicle.

An embodiment of the disclosure provides a vehicle capable of determining whether an occupant is in an abnormal state based on detection information of a plurality of detectors and transmitting rescue information to an external device in response to the abnormal state when it is determined that the occupant is in the abnormal state.

Another embodiment of the disclosure provides a vehicle capable of determining whether the vehicle is in a normal state based on detection information of a plurality of detectors when an emergency light is in a turned-on state, determining a turning-on cause of the emergency light based on current location information when it is determined that the vehicle is in the normal state, and transmitting guide information corresponding to the determined turning-on cause of the emergency light to an external device.

Additional embodiments of the disclosure will be set forth in part in the description which follows and, in part, will be obvious from the description, or may be learned by practice of the disclosure.

In accordance with an embodiment of the disclosure, a vehicle includes an emergency light, a plurality of detectors, a communication device configured to perform communication with an external device and receive current location information, and a processor configured to determine whether the vehicle is in a normal state based on detection information of the plurality of detectors when the emergency light is in a turned-on state, determine a turning-on cause of the emergency light based on the current location information received by the communication device when it is determined that the vehicle is in the normal state, and control the communication device to transmit guide information corresponding to the determined turning-on cause of the emergency light to the external device.

The vehicle may further include a camera, wherein the processor may be configured to determine whether a current location is a place where parking is possible based on the current location information, recognize a lane based on image information obtained by the camera when it is determined that the current location is a place where parking is possible, and determine the turning-on cause of the emergency light as either one of a search for a parking area and an entry into the parking area based on location information of the recognized lane.

The vehicle may further include a speed detector, wherein the processor may be configured to determine whether a vehicle body is located outside or inside the parking area based on the location information of the recognized lane, and determine the turning-on cause of the emergency light as a parking area search when it is determined that a speed detected by the speed detector exceeds a reference speed and the vehicle body is located outside the parking area.

The processor may be configured to determine the turning-on cause of the emergency light as the entry into the parking area when it is determined that the speed detected by the speed detector is slower than or equal to the reference speed and the vehicle body is located inside the parking area.

The processor may be configured to determine the turning-on cause of the emergency light as temporary parking when it is determined that the speed detected by the speed detector is slower than or equal to the reference speed and the vehicle body is located outside the parking area.

The processor may be configured to control storage of the image information obtained by the camera when it is determined that the current location is a place where parking is not practical (e.g., impossible) based on the current location information.

The vehicle may further include a speed detector, wherein the processor may be configured to determine the turning-on cause of the emergency light as temporary parking and control the communication device to transmit information on the temporary parking to another vehicle when it is determined that a speed detected by the speed detector is slower than or equal to a reference speed.

The processor may be configured to determine whether an occupant is in an abnormal state based on the detection information of the plurality of detectors when the emergency light is in a turned-off state, determine a cause of an abnormality when it is determined that the occupant is in the abnormal state, and control the communication device to transmit rescue information corresponding to the determined cause of the abnormality to the external device.

The vehicle may further include a storage device configured to store emergency contact information, wherein the processor may be configured to control the communication device to transmit the rescue information to the external device based on the emergency contact information stored in the storage device when it is determined that the occupant is in the abnormal state.

The vehicle may further include an input device, wherein the processor may be configured to store in the storage device emergency contact information that is input to the input device.

The plurality of detectors may include a first open/close detector to output a door open/close signal for opening and closing of a door, a second open/close detector to output a window open/close signal for opening and closing of a window, a dust detector to output a dust detection signal for fine dust inside the vehicle, and a temperature detector to output a temperature detection signal for a temperature inside the vehicle, and the processor may be configured to, when an engine is in a turned-off state by a user, determine the cause of the abnormality of the occupant and whether the occupant is conscious based on the door open/close signal of the first open/close detector, the window open/close signal of the second open/close detector, the dust detection signal of the dust detector, and the temperature detection signal of the temperature detector.

The vehicle may further include an airbag module, and a wiper, wherein the plurality of detectors may include a vehicle height detector to output a vehicle height detection signal for a vehicle height, and a collision detector to output a collision signal for a collision, and the processor may be configured to determine the cause of the abnormality of the occupant as immersion or injury due to an accident in response to reception of a deployment signal of the airbag module and an operation signal of the wiper.

The plurality of detectors may include a first open/close detector to output a door open/close signal for opening and closing of a door, a collision detector to output a collision signal for a collision, a coupling/separation detector to output a coupling/separation signal for coupling or separation of a seat belt, a temperature detector to output a temperature detection signal for a temperature inside the vehicle, and a fuel amount detector to output a fuel amount detection signal for detection of a fuel amount, and the processor may be configured to, when it is determined that the vehicle is in a collision state based on the collision signal of the collision detector, determine the cause of the abnormality of the occupant as an injury due to an accident and determine a degree of injury of the occupant and whether the occupant is conscious, based on the coupling/separation signal of the coupling/separation detector, the door open/close signal of the first open/close detector, the temperature detection signal of the temperature detector, and the fuel amount detection signal of the fuel amount detector.

The processor may be configured to determine whether an occupant is in an abnormal state based on the detection information of the plurality of detectors when the emergency light is in a turned-on state, determine a cause of the abnormality when it is determined that the occupant is in the abnormal state, and control the communication device to transmit rescue information corresponding to the determined cause of the abnormality to the external device.

In accordance with another embodiment of the disclosure, a vehicle includes an input device, an emergency light, a plurality of detectors, a communication device configured to perform communication with an external device and receive current location information, and a processor configured to determine whether the vehicle is in a normal state based on detection information of the plurality of detectors when the emergency light is in a turned-on state, determine a turning-on cause of the emergency light based on the current location information received by the communication device when it is determined that the vehicle is in the normal state, control the communication device to transmit guide information corresponding to the determined turning-on cause of the emergency light to the external device, determine whether an occupant is in an abnormal state based on the detection information of the plurality of detectors when a start-off command is received through the input device, determine a cause of an abnormality when it is determined that the occupant is in the abnormal state, and control the communication device to transmit rescue information corresponding to the determined cause of the abnormality to the external device.

The vehicle may further include a speed detector and a camera, wherein the processor may be configured to determine whether a current location is a place where parking is possible based on the current location information, recognize a lane based on image information obtained by the camera when it is determined that the current location is a place where parking is possible, determine whether a vehicle body is located outside or inside a parking area based on location information of the recognized lane, determine the turning-on cause of the emergency light as a parking area search when it is determined that a speed detected by the speed detector exceeds a reference speed and the vehicle body is located outside the parking area, determine the turning-on cause of the emergency light as an entry into the parking area when it is determined that the speed detected by the speed detector is slower than or equal to the reference speed and the vehicle body is located inside the parking area, and determine the turning-on cause of the emergency light as temporary parking when it is determined that the speed detected by the speed detector is slower than or equal to the reference speed and the vehicle body is located outside the parking area.

The processor may be configured to control storage of the image information obtained by the camera when it is determined that the current location is a place where parking is impractical based on the current location information.

The plurality of detectors may include a first open/close detector to output a door open/close signal for opening and closing of a door, a second open/close detector to output a window open/close signal for opening and closing of a window, a dust detector to output a dust detection signal for fine dust inside the vehicle, and a temperature detector to output a temperature detection signal for a temperature inside the vehicle, and the processor may be configured to, when an engine is in a turned-off state by a user, determine the cause of the abnormality of the occupant and whether the occupant is conscious based on signals of the first open/close detector, the second open/close detector, the dust detector, and the temperature detector.

The vehicle may further include an airbag module and a wiper, wherein the plurality of detectors may include a vehicle height detector to output a vehicle height detection signal for a vehicle height and a collision detector to output a collision signal for a collision, and the processor may be configured to determine the cause of the abnormality of the occupant as immersion or injury due to an accident in response to reception of a deployment signal of the airbag module and an operation signal of the wiper.

The plurality of detectors may include a first open/close detector to output a door open/close signal for opening and closing of a door, a collision detector to output a collision signal for a collision, a coupling/separation detector to output a coupling/separation signal for coupling or separation of a seat belt, a temperature detector to output a temperature detection signal for a temperature inside the vehicle, and a fuel amount detector to output a fuel amount detection signal for detection of a fuel amount, and the processor may be configured to, when it is determined that the vehicle is in a collision state based on the collision signal of the collision detector, determine the cause of the abnormality of the occupant as an injury due to an accident and determine a degree of injury of the occupant and whether the occupant is conscious, based on the coupling/separation signal of the coupling/separation detector, the door open/close signal of the first open/close detector, the temperature detection signal of the temperature detector, and the fuel amount detection signal of the fuel amount detector.

BRIEF DESCRIPTION OF THE DRAWINGS

These and/or other features of embodiments of the disclosure will become apparent and more readily appreciated from the following description of exemplary embodiments, taken in conjunction with the accompanying drawings, in which.

DETAILED DESCRIPTION OF ILLUSTRATIVE EMBODIMENTS

Figure 1:
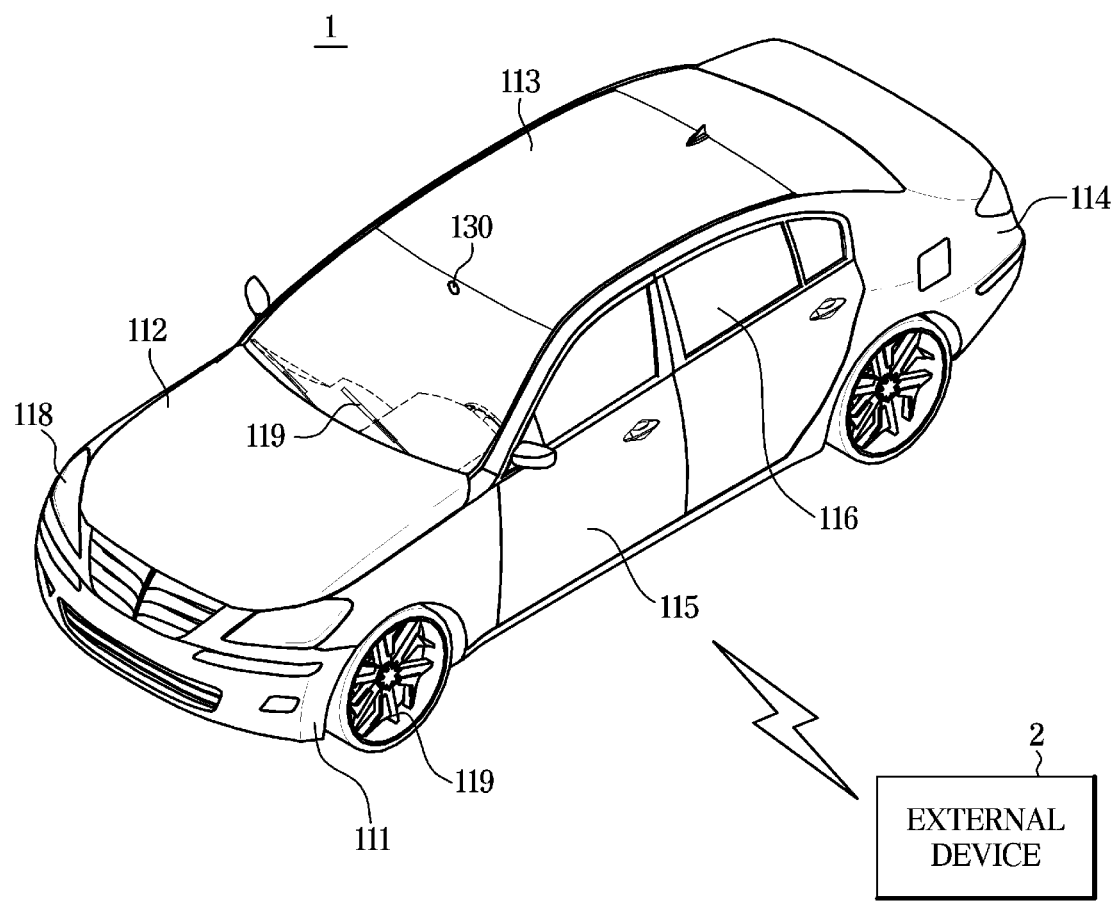
FIG. 1 is an exemplary view of a vehicle according to an embodiment.

Throughout the specification, like reference numerals refer to like elements. This specification does not describe all features of embodiments, and duplicative information between general information or embodiments in the technical field of the disclosure will be omitted. The terms 'member,' 'module,' and 'device' used in this specification may be embodied as software or hardware, and it is also possible for a plurality of 'members,' 'modules,' and 'devices' to be embodied as one component, or one 'member,' 'module,' and 'device' to include a plurality of components according to the embodiments.

Throughout the specification, when a part is referred to as being "connected" to another part, it includes not only a direct connection but also an indirect connection, and the indirect connection includes connecting through a wireless network.

Also, when it is described that a part "includes" an element, it means that the element may further include other elements, not excluding the other elements unless specifically stated otherwise.

The terms 'first,' 'second,' etc. are used to distinguish one element from another element, and the elements are not limited by the above-mentioned terms.

The singular forms "a," "an," and "the" include plural referents unless the context clearly dictates otherwise.

In each step, an identification numeral is used for convenience of explanation, the identification numeral does not describe the order of the steps, and each step may be performed differently from the order specified unless the context clearly states a particular order.

Hereinafter, the operation principle and embodiments of the disclosure will be described with reference to the accompanying drawings.

FIG. 1 is an exemplary view of a vehicle according to an embodiment.

The vehicle 1 includes a vehicle body having an interior and an exterior, and a chassis in which mechanical devices necessary for driving are installed as the remaining parts except for the vehicle body.

The vehicle body includes a front panel 111, a bonnet 112, a roof panel 113, a rear panel 114, front and rear left and right doors 115, and windows 116 operably provided on the front and rear left and right doors 115.

On the exterior of the vehicle body, a side mirror to provide a driver with a view of the rear of the vehicle 1, a wiper 117 to wipe raindrops or snow while moving left and right on a front windshield to secure a front view in case of rain or snow, and lamps to allow the driver to easily see the surroundings while keeping an eye on the front and to perform functions of signaling to and communicating with other vehicles and pedestrians are provided.

The lamps may include a high beam, a low beam, a fog lamp, a tail lamp, a brake lamp, a turn indicator lamp, a reversing lamp, a sidelight, and an emergency light.

The emergency light 118 is a lamp for notifying an emergency situation to external persons or other vehicles.

The interior of the vehicle body may include a plurality of seats on which the driver and the occupants sit, a dashboard provided in front of a driver seat and an occupant seat, a center fascia provided between the driver seat and the occupant seat, and a head unit provided between the dashboard and the center fascia, and may include seat belts respectively provided on the plurality of seats.

The chassis of the vehicle 1, which is a frame to support the vehicle body, may include a power device, a braking device, and a steering device for applying a driving force, a braking force and a steering force to front, rear, left, and right wheels 119, and further includes a suspension device, a transmission device, and the like.

The vehicle 1 may further include a camera 130 to obtain surrounding image data and an obstacle detector (not shown) to obtain obstacle data around the vehicle 1.

The obstacle detector may include at least one of a radar sensor, a lidar sensor, and an ultrasonic sensor.

One or more of the radar sensors may be provided, one or more of the lidar sensors may be provided, and one or more of the ultrasonic sensors may be provided.

The camera 130 captures the surroundings of the vehicle 1. One or more of the camera 130 may be provided.

The camera 130 may be at least one of a front camera to obtain an image of the front and a rear camera to obtain an image of the rear.

The camera 130 may obtain an image of an environment around the vehicle.

For example, the camera 130 may obtain an image of at least one of a road, another vehicle, a pedestrian, a cyclist, a lane, a curb, a guard rail, a tree, and a street lamp.

The camera 130 may include a plurality of lenses and an image sensor. The image sensor may include a plurality of photodiodes to convert light into an electrical signal, and the plurality of photodiodes may be arranged in a two-dimensional matrix.

The vehicle 1 may perform communication with an external device 2. The external device 2 may include at least one of a server, a terminal, and another vehicle.

The server may be a device provided in a government office or rescue organization that supports manpower or equipment for performing a rescue operation in response to rescue information.

The government office may include a road traffic authority, a fire station, a police station, a hospital, and an emergency medical center.

The server may be a device provided in a tow truck support center, an ambulance support center, a repair shop, an insurance company, or the like.

The terminal, which is a pre-registered terminal, may be a terminal of a user who is a vehicle owner, or may be a terminal of an acquaintance of the user. The terminal of the acquaintance may be a terminal corresponding to an emergency contact.

The terminal may be implemented as a computer or a portable terminal that may be connected to a vehicle through a network.

Herein, the computer may include, for example, a notebook, a desktop, a laptop, a tablet PC, a slate PC, and the like, on which a web browser is installed, and the portable terminal, which is a wireless communication device that ensures portability and mobility, may include all kinds of handheld based wireless communication devices, for example, such as a PCS (Personal Communication System), a GSM (Global System for Mobile communications), a PDC (Personal Digital Cellular), a PHS (Personal Handyphone System), a PDA (Personal Digital Assistant), an IMT (International Mobile Telecommunication)-2000, a CDMA (Code Division Multiple Access)-2000, a W-CDMA (W-Code Division Multiple Access), a WiBro (Wireless Broadband Internet) terminal, and a smart phone, and a wearable device such as a watch, a ring, a bracelet, an anklet, a necklace, a pair of glasses, a contact lens, and a head-mounted-device (HMD).

Figure 2:
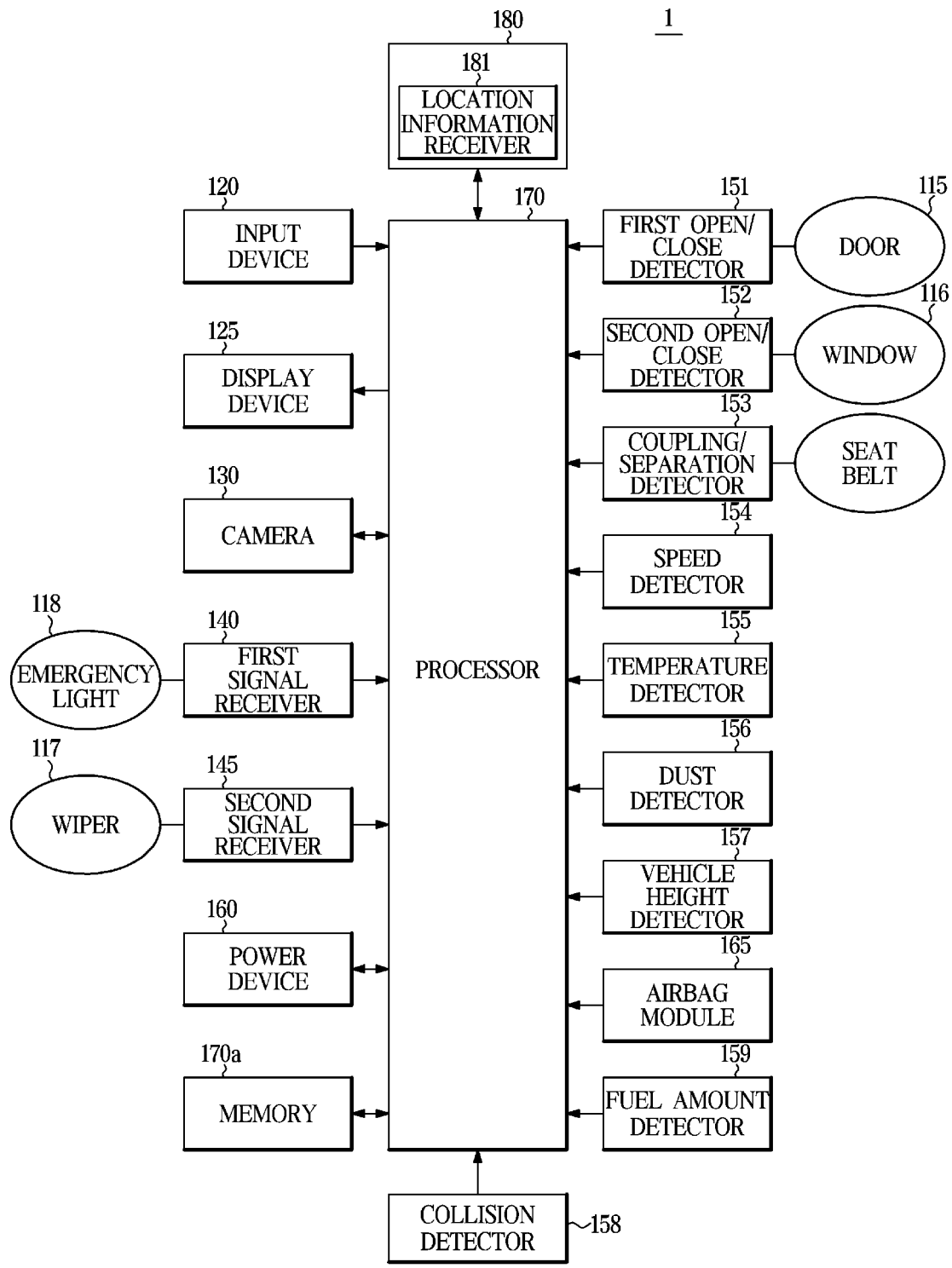
FIG. 2 is a control configuration diagram of the vehicle according to an embodiment.

FIG. 2 is a control configuration diagram of the vehicle according to an embodiment.

The vehicle 1 includes an input device 120, a display device 125, the camera 130, a first signal receiver 140, a second signal receiver 145, a plurality of detectors 151-159, a power device 160, an airbag module 165, a processor 170, a memory 170a, and a communication device 180.

The input device 120 receives a user input.

The input device 120 may receive a start-on command and a start-off command.

The input device 120 may receive a wiper operation-on command and a wiper operation-off command, and may receive an emergency light turn-on command and an emergency light turn-off command.

The input device 120 may receive a window opening command and a closing command.

The input device 120 may be provided on the head unit or the center fascia in the vehicle 1, and or may be provided on a vehicle terminal (not shown, an audio video navigation device (AVN device)).

The input device 120 may receive emergency contact information to be contacted in a rescue situation.

There may be one or more of the emergency contacts.

Priority per emergency contact may be given to respond to a selection of the user. That is, the emergency contact may include information about a name, phone number, and priority.

In a rescue situation, the input device 120 may receive the name of an insurance company subscribed to, and may receive contact information of the insurance company.

The input device 120 may receive at least one of a phone number, an email address, and a website link address for an emergency contact.

The input device 120 may include a hardware device such as various buttons or switches, a pedal, a keyboard, a mouse, a track-ball, various levers, and a handle or a stick.

Also, the input device 120 may include a graphical user interface (GUI) such as a touch pad, that is, a software device. The touch pad may be implemented as a touch screen panel (TSP) to form a mutual layer structure with the display device.

When configured as the touch screen panel (TSP) forming a mutual layer structure with the touch pad, the display device may also be used as an input device.

The display device 125 may display operation information on a function being performed in the vehicle. For example, the display device 125 may display information related to a phone call, display information about content output through a user terminal (not shown), or display information related to music reproduction, and displays external broadcast information.

The display device 125 may display information of an emergency contact.

The display device 125 displays map information, and may display map information and route guide information in which a route to a destination is matched.

The display device 125 may also display abnormal state information and normal state information of the vehicle.

The display device 125 may display an image obtained by the camera 130.

The display device 125 may include a lamp such as an LED.

The display device 125 may include a cathode ray tube (CRT), a digital light processing (DLP) panel, a plasma display panel, a liquid crystal display (LCD) panel, an electro luminescence (EL) panel, an electrophoretic display (EPD) panel, an electrochromic display (ECD) panel, a light emitting diode (LED) panel or an organic light emitting diode (OLED) panel, but is not limited thereto.

The display device 125 may include a cluster provided in the vehicle 1.

The cluster may include a lamp for displaying a variety of driving information related to driving of the vehicle. Such a cluster may turn on or turn off the lamp in response to a control command of the processor 170.

The camera 130 obtains an image of an environment around the vehicle.

The camera 130 may be provided on the front windshield inside the vehicle, may be provided on a rearview mirror inside the vehicle, or may be provided on the roof panel 113 to be exposed to the outside.

The camera 130, which is a device to detect object information and convert the detected object information into an electrical image signal, detects object information on the front, left and right sides of the vehicle in an environment outside the vehicle at the current location of the vehicle, in particular, a road on which the vehicle travels and surroundings thereof, and transmits image information of the detected object to the processor 170.

The camera 130 may include a front camera to obtain an image of the front of the vehicle, and may include at least one of a left camera and a right camera to obtain images of the left and right sides of the vehicle, and a rear camera to obtain an image of the rear of the vehicle.

The camera 130 may be a rotatable camera.

The camera 130 may include a CCD or CMOS image sensor, and may include a 3D spatial recognition sensor such as a KINECT (RGB-D sensor), a TOF (Structured Light Sensor), and a stereo camera.

The camera 130 may be a camera for a black box, and may be an autonomous driving camera for autonomous driving or a camera for detecting obstacles.

The camera 130 may include a camera of a surrounding monitoring device (SVM: Surround View Monitor, or AVM), and may include a camera of a blind spot detection device (BSD) or a camera of a rear detection device.

The camera 130 may be a wide-angle camera.

The first signal receiver 140 may be connected to the emergency light 118 to receive a turned-on signal corresponding to a turned-on state of the emergency light 118. The first signal receiver 140 may not receive a signal or may receive a turned-off signal upon the emergency light 118 being in a turned-off state.

The turned-on signal may be an ON signal, a voltage signal having a predetermined magnitude or more, or a current signal having a predetermined magnitude or more.

The emergency light 118 may be turned on in response to the turn-on command received from the input device 120, and may be turned off in response to the turn-off command received from the input device 120.

The emergency light 118 may be automatically turned on in an emergency situation in response to the control command of the processor 170.

The second signal receiver 145 may be connected to the wiper 117 to receive an operation signal upon the wiper 117 being in an operating state. The second signal receiver 145 may not receive a signal or may receive an OFF signal upon the wiper 117 being in a stopped state.

The operation signal may be an ON signal, a voltage signal having a predetermined magnitude or more, or a current signal having a predetermined magnitude or more.

The wiper 117 may operate in response to an operation command received from the input device 120, may stop in response to a stop command received from the input device 120, and may adjust a speed moving left and right in response to a moving speed adjusting command received from the input device 120.

The wiper 117 may automatically operate or stop, and may adjust the speed moving left and right, based on the control command of the processor 170.

The wiper 117 may adjust the moving speed to a speed in response to an amount of rain or snow based on the control command of the processor 170.

The plurality of detectors 151-159 includes a first open/close detector 151, a second open/close detector 152, a coupling/separation detector 153, a speed detector 154, a temperature detector 155, a dust detector 156, a vehicle height detector 157, a collision detector 158, and a fuel amount detector 159.

The first open/close detector 151 detects opening or closing of the door 115, outputs a door open signal in response to the opening of the door, and outputs a door closing signal in response to the closing of the door 115.

The first open/close detector 151 may be provided on each of the plurality of doors 115. That is, a plurality of the first open/close detectors 151 may be provided.

The second open/close detector 152 detects opening or closing of the window 116, outputs a window open signal in response to the opening of the window 116, and outputs a window closing signal in response to the closing of the window 116.

The second open/close detector 152 may be provided on each of the plurality of windows 16. That is, a plurality of the second open/close detectors 152 may be provided.

The coupling/separation detector 153 detects coupling or separation of the seat belt.

The coupling/separation detector 153 may output a coupling signal in response to the coupling of the seat belt and may output a separation signal in response to the separation of the safety belt.

Hereinafter, the coupling signal and the separation signal will be described as a coupling/separation signal.

The coupling/separation detector 153 may be provided on each of the plurality of seat belts. That is, a plurality of the coupling/separation detectors 153 may be provided.

The seat belt is provided on each of the plurality of seats, and protects the occupant by allowing the occupant to be seated in the seat in the event of a collision.

The speed detector 154 detects the speed of the vehicle and outputs speed information on the detected speed.

The speed detector 154 may include a plurality of wheel speed sensors. The speed detector 154 may include an acceleration sensor. The speed detector 154 may include a plurality of wheel speed sensors and an acceleration sensor.

When the speed detector 154 is implemented as an acceleration sensor, the processor 170 may obtain an acceleration of the vehicle 1 based on longitudinal acceleration information detected by the acceleration sensor and may obtain the driving speed of the vehicle 1 based on the obtained acceleration.

When the speed detector 154 is implemented as an acceleration sensor and a plurality of wheel speed sensors, the processor 170 may obtain the driving speed of the vehicle 1 based on the acceleration information detected by the acceleration sensor and wheel speed information obtained by the plurality of wheel speed sensors.

The temperature detector 155 is provided in the interior of the vehicle 1 and outputs a temperature detection signal in response to a temperature inside the vehicle 1.

The dust detector 156 detects an amount of fine dust inside the vehicle and outputs a dust detection signal in response to the detected amount of fine dust.

The dust detector 156 may include a laser optical fine dust sensor.

The laser optical fine dust sensor may detect concentrations of fine dust of PM10, ultrafine dust of PM2.5, and dust of PM1.0 which is smaller than the ultrafine dust, respectively.

The vehicle height detector 157 detects a relative position change (a change in height of the vehicle) of a rear axle of the vehicle body and outputs a detected vehicle height detection signal.

The vehicle height detector 157 may output inclination information with respect to a front-rear direction of the vehicle body. The inclination information may be angle information.

The vehicle height detector 157 may be a sensor that detects a state of the rear of the vehicle, that is, a height of the vehicle such as bouncing and pitching.

The vehicle height detector 157 may include an optical sensor. That is, the vehicle height detector 157 may include a light emitting diode, a phototransistor, and a slit plate. In this case, the vehicle height detector 157 detects a change in vehicle height at the rear while a slit installed on a disk plate turns a light on and off.

The vehicle height detector 157 may be a variable resistor. In this case, the vehicle height detector 157 outputs an output value in which a resistance value changes depending on the vehicle height as information on the vehicle height.

The vehicle height detector 157 may detect an AC voltage output from a slide pipe that performs a linear motion depending on the change in vehicle height, and may output the detected AC voltage as information on the vehicle height.

The collision detector 158 outputs a collision signal in response to whether the vehicle collides.

The collision detector 158 may include a yaw rate sensor to output a speed signal in which a rotation angle (yaw angle) changes around a vertical line passing through the center of the vehicle and a lateral acceleration sensor to output a lateral acceleration signal.

The collision detector 158 may be at least one of a pressure sensor, a force sensor, a limit switch, a proximity sensor, an Arduino shock sensor, a vibration sensor, and a touch sensor. However, the collision detector 158 is not limited thereto.

The fuel amount detector 159 detects a fuel amount in a fuel tank.

The fuel amount detector 159 may be a fuel weight sensor to detect a weight of fuel, and may be a level sensor to detect a level of fuel in the fuel tank.

The vehicle may optionally include a rain detector to detect whether or not there is precipitation and an amount of precipitation.

The rain detector is provided on the wiper 117 or the front windshield, and outputs whether or not precipitation is present and detection information (i.e., information on whether or not precipitation is present and information on the detected amount of precipitation) corresponding to the amount of precipitation (amount of rainwater), respectively.

The vehicle may further include a gas detector to detect a concentration of a gas harmful to the human body among gases inside the vehicle.

The gas may include at least one of carbon dioxide, carbon monoxide, sulfur dioxide, nitrogen dioxide, ammonia, hydrogen sulfide, hydrogen chloride, ethylene oxide, and ethylene.

The vehicle may further include an occupant detector to detect an occupant of each seat and output detected occupant information to recognize the presence of occupants in the vehicle and the number of occupants.

The occupant detector may be provided on at least one of the seat and the seat belt of the vehicle.

For example, the occupant detector may include at least one of a weight detector, a pressure detector, a capacitance detector, and the coupling/separation detector 153 of the seat belt.

The occupant detector may include a camera provided inside the vehicle.

The power device 160, which is a device that generates a driving force for a vehicle, may perform an operation in response to the start-on command received by the input device 120, and may perform a stop in response to the start-off command received by the input device 120.

The power device 160 is a power train.

The power device 160 may be stopped due to an accident.

In the case of a vehicle with an internal combustion engine, the power device may include an engine.

In the case of an electric vehicle, the power device may include a motor and a battery.

In the case of a hybrid vehicle, the power device may include a motor, a battery and an engine.

The airbag module 165, which is a protective bag mounted in front of the occupant, is a device to detect an impact force when the vehicle collides and inflate the bag with compressed gas to alleviate the impact on the occupant.

The airbag module 165 is for the safety of the occupant in the event of a vehicle collision.

The airbag module 165 may include a plurality of airbag devices respectively provided in different spaces inside the vehicle. Each of the airbag devices may transmit a deployment signal to the processor 170 upon deployment.

The vehicle may further include a signal receiver of a shift lever to receive location information of the shift lever.

The signal receiver of the shift lever receives an operation signal of the shift lever and transmits an operation signal of the shift lever corresponding to the received operation signal to the processor 170.

The operation signal of the shift lever includes signals corresponding to a parking stage (P stage), a neutral stage (N stage), a forward driving stage (D stage), and a reverse driving stage (R stage).

When the turned-on signal is received through the first signal receiver 140, the processor 170 determines that the emergency light is in the turned-on state, determines whether the emergency light is in the turned-on state in response to input of the user or whether the emergency light is in the turned-on state in response to a braking force applied through a brake pedal.

When it is determined that the emergency light is in the turned-on state in response to the input of the user, the processor 170 determines whether the vehicle is in a normal state based on detection information of the plurality of detectors.

The processor 170 may determine whether the emergency light turn-on command is received through the input device 120, and may determine whether the vehicle is in the normal state based on the detection information of the plurality of detectors when it is determined that the emergency light turn-on command is received through the input device 120.

That is, the processor 170 determines a turning-on cause of the emergency light based on the current location information received in the communication device 180 when it is determined that the vehicle is the normal state, and controls the communication device 180 to transmit guide information corresponding to the determined turning-on cause of the emergency light to the external device 2.

More specifically, the processor 170 determines whether the current location is a place where parking is possible based on the current location information, recognizes a lane based on image information obtained by the camera 130 when it is determined that the current location is a place where parking is possible, and determines the turning-on cause of the emergency light based on location information of the recognized lane as either one of a search for a parking area and an entry into the parking area.

The place where parking is possible may include a parking lot and a rest area.

The processor 170 determines whether the vehicle body is located outside or inside the parking area based on the location information of the recognized lane. The processor 170 determines the turning-on cause of the emergency light as a parking area search when it is determined that the driving speed of the vehicle exceeds a reference speed and the vehicle body is located outside the parking area based on the speed information detected by the speed detector 154 and the vehicle body is located outside the parking area. In this case, the processor 170 does not transmit the rescue information to the external device 2 even when the emergency light is in the turned-on state.

The processor 170 determines the turning-on cause of the emergency light as the entry into the parking area when it is determined that the driving speed of the vehicle 1 is lower than or equal to the reference speed based on the speed information detected by the speed detector 154 and the vehicle body is located inside the parking area. In this case, the processor 170 may transmit guide information for guiding the entry into the parking area to other nearby vehicles.

The processor 170 determines that cause of the turning-on of the emergency light is due to temporary parking when it is determined that the driving speed of the vehicle 1 is lower than or equal to the reference speed based on the speed information detected by the speed detector 154 and the vehicle body is located outside the parking area. In this case, the processor 170 may transmit guide information for guiding the temporary parking to other nearby vehicles. The temporary parking is a parking state in which the parking time of the vehicle is approximately 5 minutes or less.

The processor 170 controls storage of the image information obtained by the camera 130 when it is determined that the current location is a place where parking is impractical (e.g., impossible) based on the current location information. In this case, the processor 170 may transmit guide information for guiding emergency parking to other nearby vehicles.

The processor 170 may determine that the driving speed of the vehicle 1 is lower than or equal to the reference speed based on the speed information detected by the speed detector 154, determine the turning-on cause of the emergency light as the temporary parking, and transmit the guide information for guiding the temporary parking to other nearby vehicles.

The processor 170 determines whether the occupant is in the abnormal state based on the detection information of the plurality of detectors when the emergency light is in the turned-off state, determines a cause of the abnormality when it is determined that the occupant is in the abnormal state, and controls the communication device 180 to transmit rescue information corresponding to the determined cause of the abnormality to the external device 2.

The processor 170 may control the communication device 180 to transmit the rescue information to the external device 2 based on the emergency contact information stored in a storage device when it is determined that the occupant is in the abnormal state.

The processor 170 may also control the storage of the received emergency contact information when the emergency contact information is received through the input device 120.

The processor 170 may, when the engine is in a start-off state by the user, determine the cause of the abnormality of the occupant and whether the occupant is conscious based on a door open/close signal of the first open/close detector 151, a window open/close signal of the second open/close detector 152, the dust detection signal of the dust detector 156, and the temperature detection signal of the temperature detector 155.

The processor 170 may determine the cause of the abnormality of the occupant as immersion or injury due to an accident in response to reception of the airbag module deployment signal and a wiper operation signal.

The processor 170 may determine that the wiper 117 is in operation when the wiper operation signal is received through the second signal receiver 145.

The processor 170 may determine whether the wiper 117 is in the operating state in response to a user command through the input device 120 or whether the wiper 117 is in the operating state in response to a detection signal of the rain detector.

The processor 170 may determine that the vehicle 1 is in a submerged state when it is determined that the wiper 117 is automatically operated in response to the detection signal of the rain detector, and in this case, may determine that the cause of the abnormality of the occupant is due to immersion.

The processor 170 may, when it is determined that the vehicle 1 is in a collision state based on the collision signal of the collision detector 158, determine the cause of the abnormality of the occupant as an injury due to an accident and determine the degree of injury of the occupant and whether the occupant is conscious based on the coupling/separation signal of the coupling/separation detector 153, the door open/close signal of the first open/close detector 151, the temperature detection signal of the temperature detector 155, and a fuel amount detection signal of the fuel amount detector 159.

The processor 170 may determine whether the occupant is in the abnormal state based on the detection information of the plurality of detectors when the emergency light is in the turned-on state, determine the cause of the abnormality when it is determined that the occupant is in the abnormal state, and control the communication device 180 to transmit the rescue information corresponding to the determined cause of the abnormality to the external device 2.

The processor 170 may determine whether the occupant is in the abnormal state based on the detection information of the plurality of detectors when an engine start-off command is received through the input device 120, determine the cause of the abnormality when it is determined that the occupant is in the abnormal state, and control the communication device 180 to transmit the rescue information corresponding to the determined cause of the abnormality to the external device 2.

The processor 170 may also determine whether the vehicle collides based on a yaw rate signal and the lateral acceleration signal detected by the collision detector 158.

The processor 170 may also control the operation of the wiper based on the detection signal of the rain detector, determine an amount of water on the front windshield based on the detection signal of the rain detector, and adjust the moving speed of the wiper 117 based on the determined amount of water.

The processor 170 may also control an automatic turning-on of the emergency light based on the braking force applied to the brake pedal.

A configuration for the determination of the cause of the turning-on of the emergency light and the transmission of the guide information will be described with reference to FIG. 4.

A configuration for the determination of the abnormality of the occupant and the transmission of the rescue information will be described with reference to FIGS. 5A, 5B and 6.

At least one component may be added or deleted in consideration of the performance of the processor 170 illustrated in FIG. 2. It will be readily understood by those skilled in the art that the mutual positions of the components may be changed in consideration of the performance or structure of the processor 170.

Figure 3:
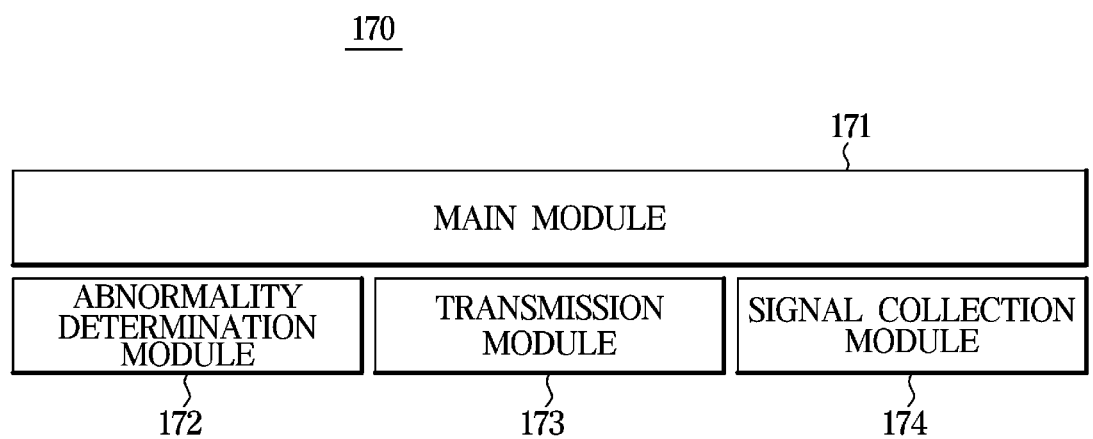
FIG. 3 is a detailed configuration diagram of a processor provided in the vehicle according to an embodiment.

As illustrated in FIG. 3, the processor 170 may include a main module 171 to control each module, a signal collection module 174 to collect signals output from the plurality of detectors, an abnormality determination module 172 to determine whether the vehicle 1 and the occupant are in the abnormal state based on the signals collected by the signal collection module 174, and a transmission module 173 to transmit the rescue information and guide information in response to the state of the vehicle 1 and the occupant.

Each of the modules illustrated in FIG. 3 means a software component and/or a hardware component such as a field programmable gate array (FPGA) and an application specific integrated circuit (ASIC).

The above electronic components may communicate with each other through a vehicle communication network NT. For example, the electronic components may transmit and receive data using Ethernet, MOST (Media Oriented Systems Transport), Flexray, CAN (Controller Area Network) and/or LIN (Local Interconnect Network).

The memory 170a stores the map information and may store a phone number related to the emergency contact and a link address of a web page related to the police station or the fire station.

The link address of the web page related to the police station or the fire station may be a link for transmitting accident information.

The memory 170a stores a phone number of the user, an email of the user, and phone numbers and emails of persons registered by the user.

The memory 170a may store image information obtained in response to the turning-on of the emergency light.

The image stored in the memory 170a may be a moving image or a snapshot image.

Images stored in the memory 170a may be classified by date and may be stored together with location information.

The memory 170a may also delete stored images in response to the control command from the processor 170.

The memory 170a may also store a storage period of an image for permanently deleting the stored image.

The memory 170a may store various data for the overall operation of the vehicle 1, such as a program for processing or controlling the processor 170.

The communication device 180 may transmit the guide information and the rescue information to the external device 2 in response to the control command of the processor 170.

The communication device 180 may transmit an image stored in the memory 170a to the external device 2 in response to the control command of the processor 170.

The external device 2 may include at least one of a server of the police station or the fire station, a server of the emergency medical center, a pre-registered terminal, and another vehicle.

The external device 2 may be a telematics server of a vehicle manufacturer, a server of a vehicle service center, a cloud server, and a web hard server.

The communication device 180 performs communication between various electronic devices inside the vehicle 1 and communication with the external device 2. The communication device 180 may perform communication between vehicles (V2V) and communication with an infrastructure or server (V2X).

The communication device 180 may include one or more components that enable communication between external devices, and may include, for example, at least one of a short-range communication module, a wired communication module, and a wireless communication module.

The short-range communication module may include various short-range communication modules that transmit and receive signals using a wireless communication network in a short distance such as a Bluetooth module, an infrared communication module, an RFID (Radio Frequency Identification) communication module, an NFC (Near Field Communication) module, and a Zigbee communication module.

The wired communication module may include various cable communication modules such as a USB (Universal Serial Bus), an HDMI (High Definition Multimedia Interface), a DVI (Digital Visual Interface), an RS-232 (recommended standard 232), a power line communication, and a POTS (plain old telephone service), as well as various wired communication modules such as a CAN (Controller Area Network) communication module, a LAN (Local Area Network) module, a WAN (Wide Area Network) module, and a VAN (Value Added Network) module.

The wireless communication module, in addition to a Wi-Fi module and a wireless broadband module, may include wireless communication modules that support various wireless communication methods such as a GSM (Global System for Mobile Communication), a CDMA (Code Division Multiple Access), a WCDMA (Wideband Code Division Multiple Access), a UMTS (Universal Mobile Telecommunications System), a TDMA (Time Division Multiple Access), and LTE (Long Term Evolution).

The communication device 180 includes a location information receiver 181 to receive location information for recognizing a current location of the vehicle 1.

The location information receiver 181 may be a global positioning system (GPS) receiver that performs communication with a plurality of GPS satellites. The GPS receiver includes an antenna module for receiving signals from the plurality of GPS satellites and may include software for obtaining the current location using distance and time information corresponding to location signals from the plurality of GPS satellites and an output device for outputting the obtained location information of the vehicle 1.

Figure 4:
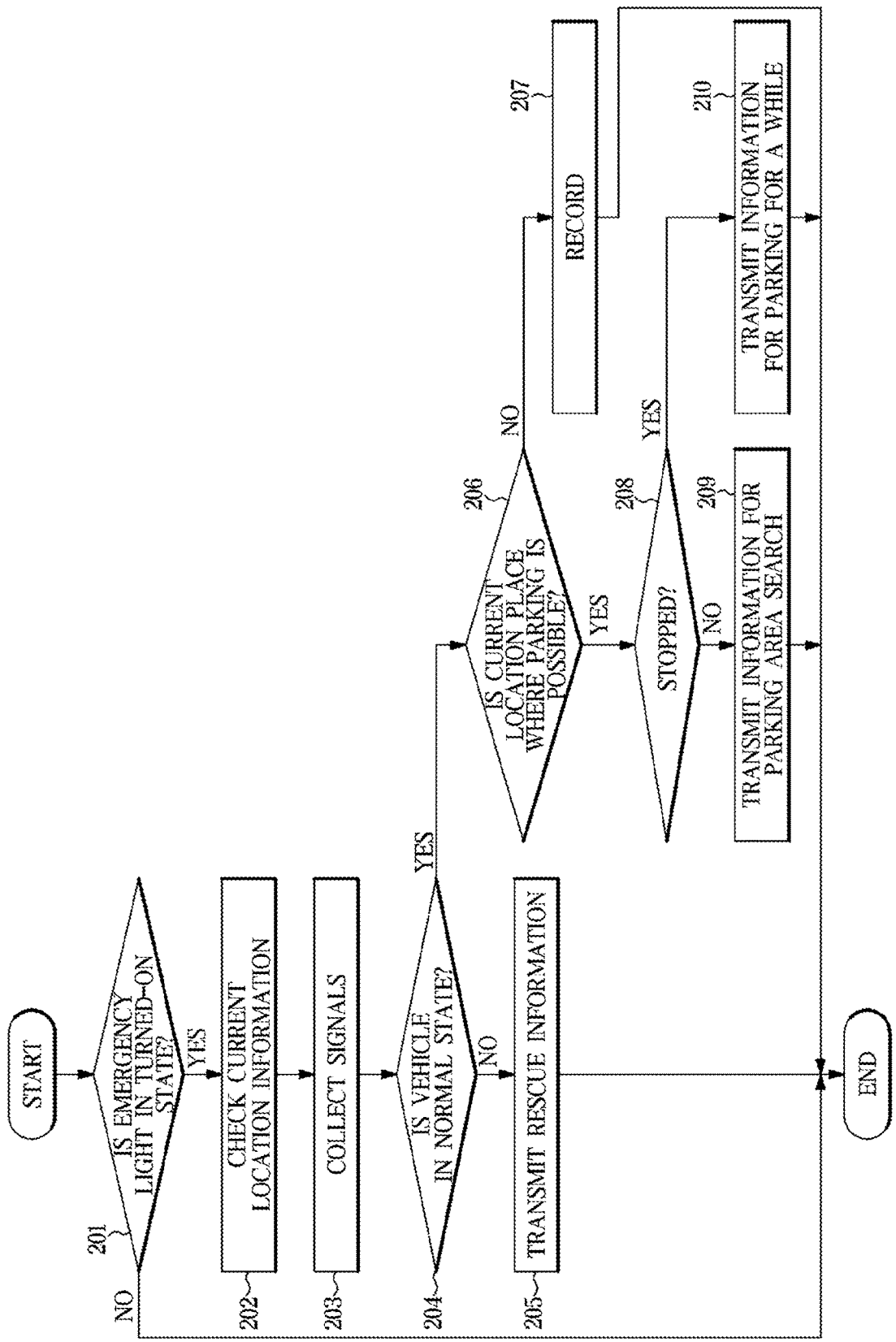
FIG. 4 is a control flowchart of the vehicle according to an embodiment.

FIG. 4 is a control flowchart of the vehicle according to an embodiment.

FIG. 4 is a flowchart for determining a cause of turning-on of the emergency light of the vehicle 1 and transmitting guide information.

The vehicle 1 determines whether the emergency light is in a turned-on state (201). In this case, the vehicle 1 determines whether the emergency light is in the turned-on state in response to a user input.

The vehicle 1 checks the current location information when it is determined that the emergency light is in the turned-on state (202).

The vehicle 1 collects signals output from the plurality of detectors (203).

The vehicle 1 may determine a state of the vehicle 1 based on at least one of a door open/close signal of the first open/close detector 151, a window open/close signal of the second open/close detector 152, a seat belt coupling/separation signal of the coupling/separation detector 153, a speed signal of the speed detector 154, a temperature detection signal of the temperature detector 155, a dust detection signal of the dust detector 156, a vehicle height detection signal of the vehicle height detector 157, a collision detection signal of the collision detector 158, and a fuel amount detection signal of the fuel amount detector 159.

The vehicle 1 determines whether the vehicle 1 is in a normal state based on the collected signals (204).

The vehicle 1 determines a state of the occupant based on the collected signals when it is determined that the vehicle 1 is not in the normal state, and determines a cause of an abnormality of the occupant and transmits rescue information when it is determined that the occupant is in an abnormal state (205).

The vehicle 1 determines whether a current location in current location information is a place where parking is possible (206) and obtains a surrounding image using the camera 130 when it is determined that the current location is a place where parking is not practical and stores the obtained image information (207). That is, the vehicle 1 performs recording using the camera 130. In this case, the vehicle 1 may transmit guide information for guiding emergency parking to other nearby vehicles.

The place where parking is possible may include a parking lot and a rest area.

The vehicle 1 recognizes a lane based on the image information obtained through the camera 130 when it is determined that the current location is a place where parking is possible, determines a parking area based on location information of the recognized lane, and determines whether the vehicle body is located outside or inside the parking area based on location information of the determined parking area.

The vehicle 1 determines whether the driving speed of the vehicle 1 exceeds the reference speed based on the speed information detected by the speed detector 154 (208). The reference speed may be 0 km/h.

That is, when the driving speed of the vehicle exceeds the reference speed, it means that the vehicle is in a driving state.

When the driving speed of the vehicle is slower than the reference speed, it means that the vehicle is in a stopped state.

The vehicle 1 determines that the turning-on cause of the emergency light is because of a parking area search when it is determined that the vehicle 1 is in the driving state and the vehicle body is located outside the parking area and transmits guide information for the parking area search to other nearby vehicles (209).

The vehicle 1 determines that the turning-on cause of the emergency light is because of the temporary parking when it is determined that the vehicle 1 is in a stopped state and the vehicle body is located outside the parking area and may transmit guide information for the temporary parking to other nearby vehicles (210).

In addition, the vehicle 1 determines that the turning-on cause of the emergency light is because of an entry into the parking area when it is determined that the vehicle 1 is in a stopped state and the vehicle body is located inside the parking area and may transmit guide information for the entry into the parking area to other nearby vehicles.

Figure 5A:
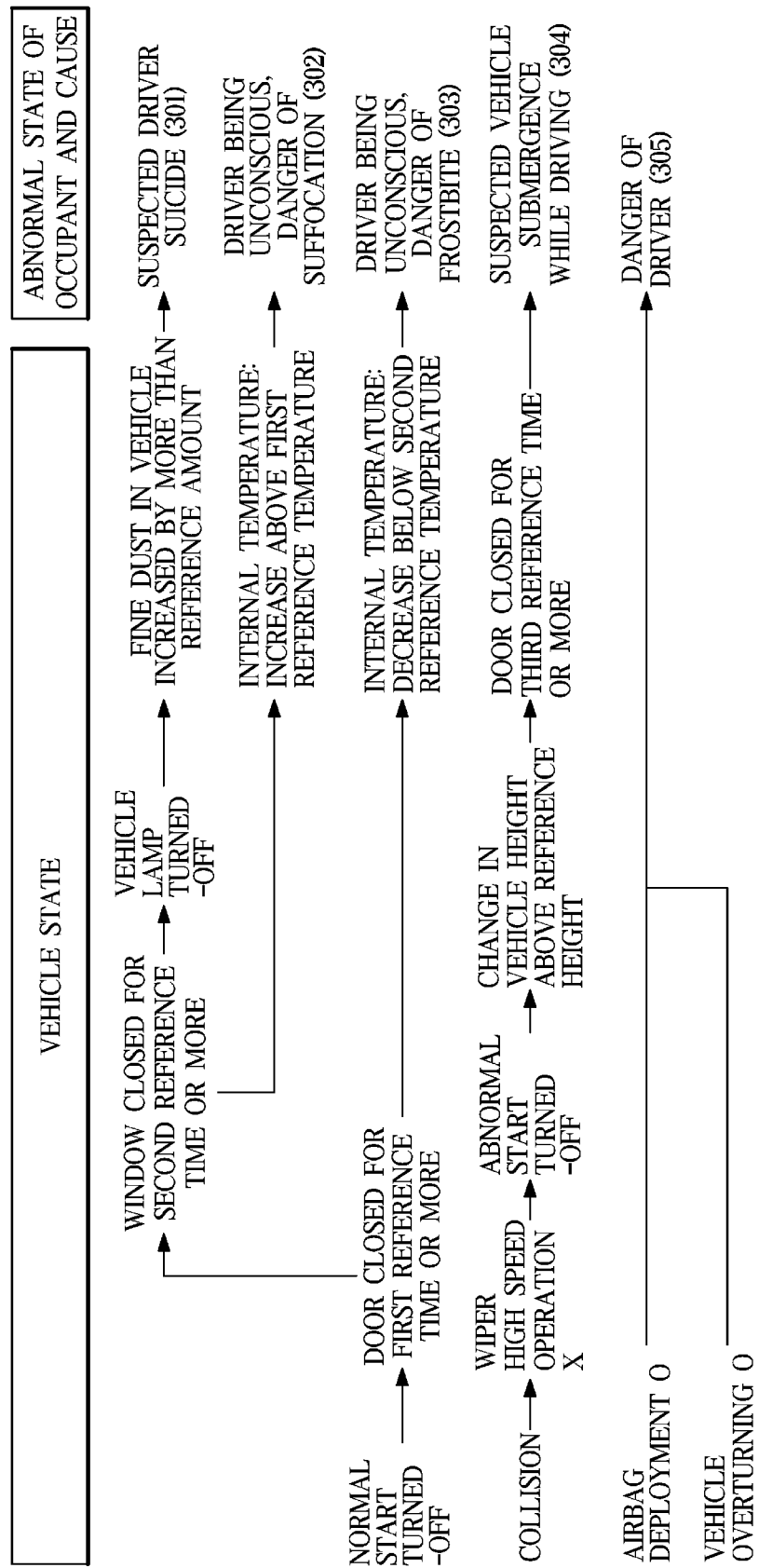
FIGS. 5A and 5B are exemplary diagrams for determining a cause of an abnormal state of an occupant in the vehicle according to an embodiment.
Figure 5B:
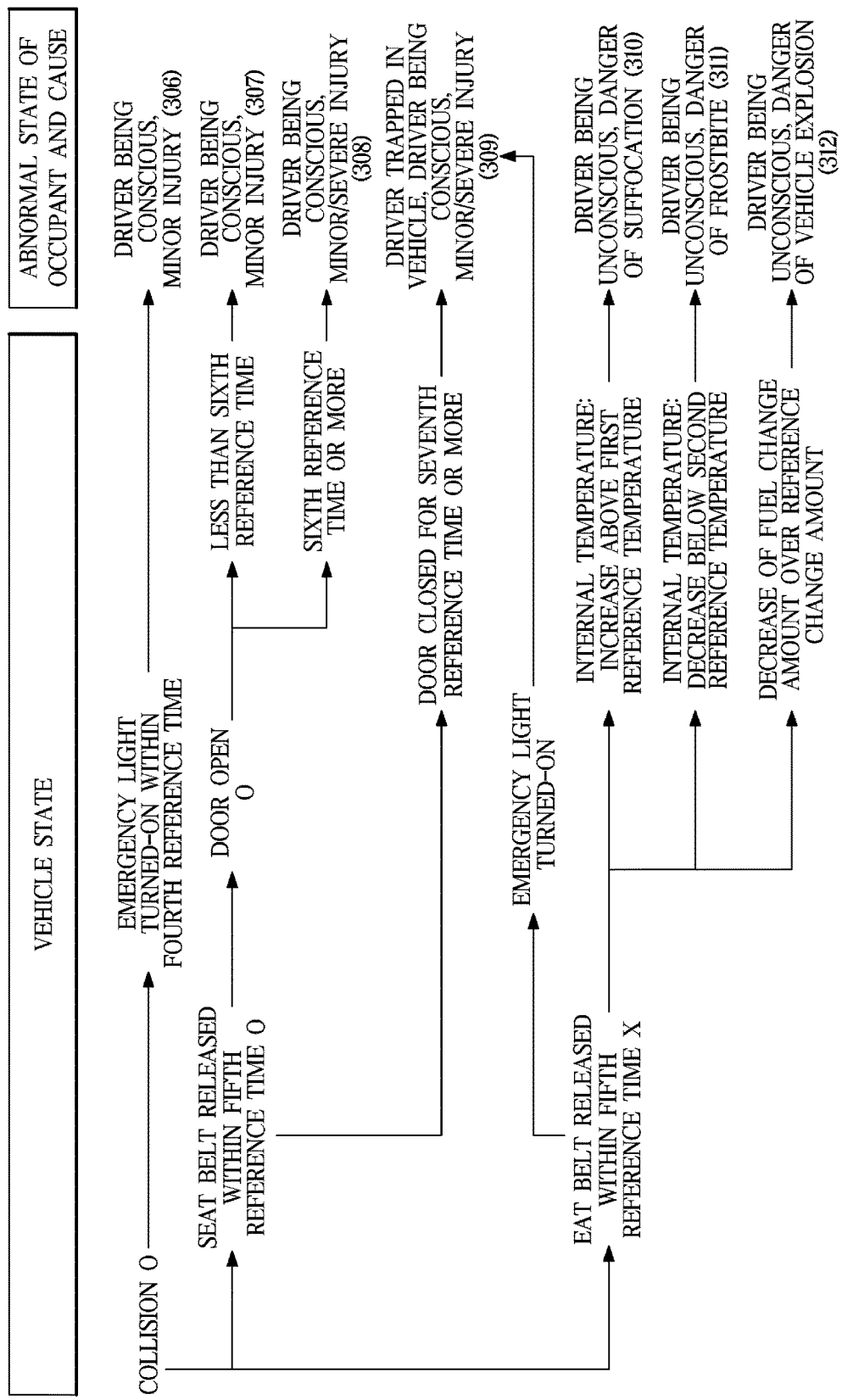
Figure 6:
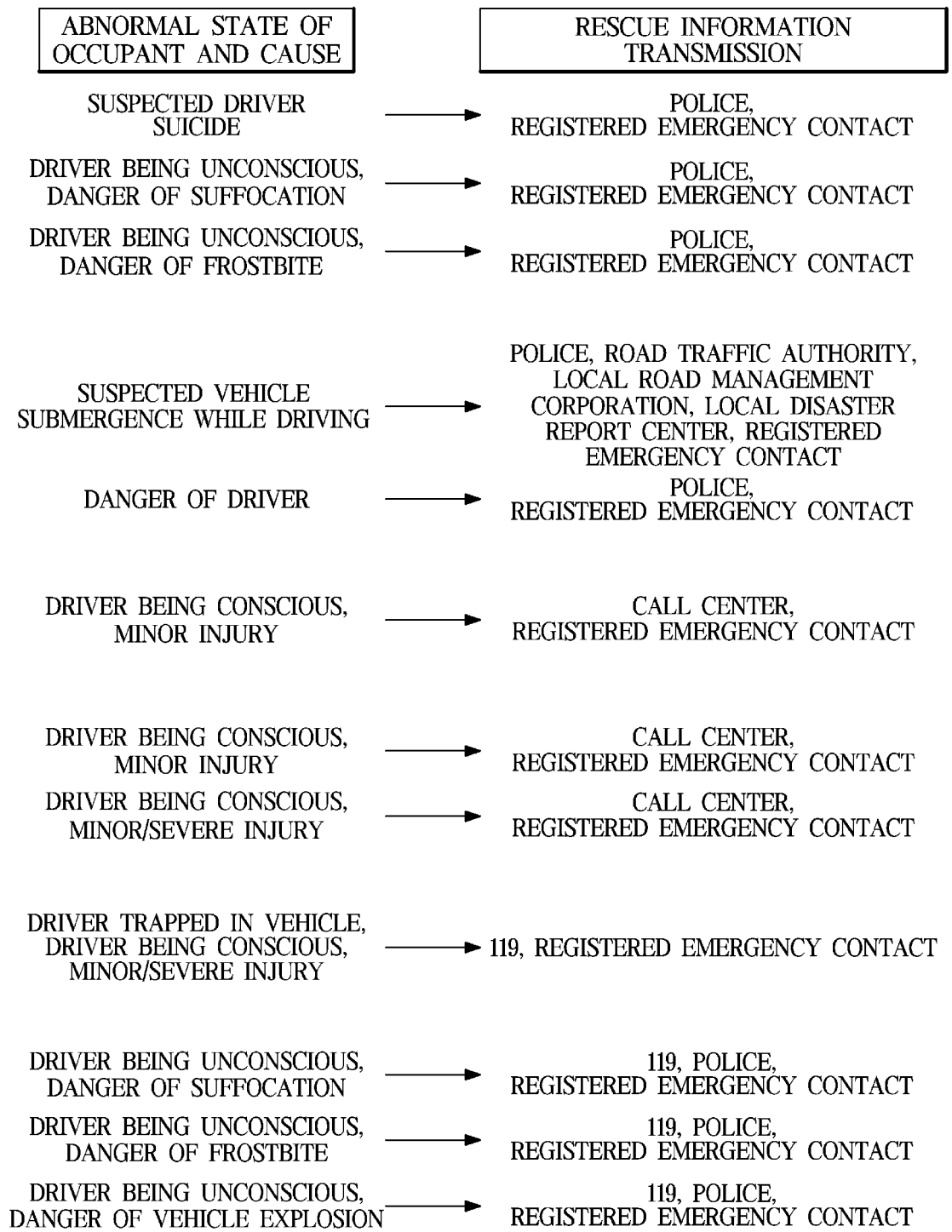
FIG. 6 is an exemplary diagram for transmitting rescue information from the vehicle according to an embodiment.

FIGS. 5A and 5B are exemplary diagrams for determining a cause of an abnormal state of an occupant according to an embodiment, and FIG. 6 is an exemplary diagram for transmitting rescue information according to an embodiment.

The vehicle 1 may determine whether a start-off command is received through the input device 120, and may determine whether the start of the vehicle 1 is normally turned off or abnormally turned off in response to whether the start-off command of the input device 120 is received.

The vehicle 1 may determine whether the door 115 is in a closed state based on the door open/close signal of the first open/close detector 151 when it is determined that the start is normally turned off, check a door closing time when it is determined that the door 115 is in the closed state, determine whether the window 116 is in a closed state based on the window open/close signal of the second open/close detector 152 when it is determined that the checked door closing time is equal to or longer than a first reference time, check a window closing time when it is determined that the window 116 is in the closed state, determine whether the lamp is turned on or off when it is determined that the checked window closing time is equal to or longer than a second reference time, determine whether an amount of dust inside the vehicle 1 is equal to or greater than a reference amount based on the dust detection signal of the dust detector 156 when it is determined that the lamp is in a turned-off state, and determine the abnormal state of the occupant as a suicide state when it is determined that the amount of dust inside the vehicle 1 is equal to or greater than the reference amount (301).

The vehicle 1 may determine whether an internal temperature is equal to or higher than a first reference temperature based on the temperature detection signal of the temperature detector 155 when the door closing time is equal to or longer than the first reference time and the window closing time is equal to or longer than the second reference time, determine the abnormal state of the driver as an unconscious state when it is determined that the internal temperature is equal to or higher than the first reference temperature, and determine that a danger factor that puts the occupant in danger is suffocation (302).

The vehicle 1 may determine whether the door 15 is in the closed state based on the door open/close signal of the first open/close detector 151 when it is determined that the start is normally turned off, check the door closing time when it is determined that the door 115 is in the closed state, determine whether the internal temperature is lower than or equal to the second reference temperature based on the temperature detection signal of the temperature detector 155 when it is determined that the checked door closing time is equal to or longer than the first reference time, determine the abnormal state of the driver (that is, the occupant) as the unconscious state when it is determined that the internal temperature is lower than or equal to the second reference temperature, and determine that the danger factor that puts the occupant in danger is frostbite (303).

The vehicle 1 may determine a state of the vehicle as a breakdown state or an accident state when it is determined that the start is abnormally turned off.

The vehicle 1 may determine whether the vehicle 1 collides based on the collision detection signal of the collision detector 158, determine whether the vehicle height is changed to be equal to or higher than a reference vehicle height based on the vehicle height detection signal of the vehicle height detector 157 when the wiper operation signal is received and a high-speed operation signal is received in the state where the vehicle 1 does not collide, determine whether the door 115 is in the closed state based on the door open/close signal of the first open/close detector 151 when it is determined that the vehicle height is changed to be equal to or higher than the reference vehicle height, check the door closing time when it is determined that the door 115 is in the closed state, and determine that the vehicle 1 is in a submerged state when it is determined that the checked door closing time is equal to or longer than a third reference time (304).

The vehicle 1 may determine the abnormal state of the driver as the submerged state.

The wiper operation signal may include a high-speed operation signal for making the wiper move faster than a preset moving speed.

The vehicle 1 may determine whether the vehicle 1 collides based on the collision detection signal of the collision detector 158 and determine the abnormal state of the driver as a dangerous state when a collision of the vehicle 1 occurs or a deployment signal is received from the airbag module 165.

The vehicle 1 may determine the abnormal state of the driver as the dangerous state when it is determined that the vehicle height is equal to or higher than the reference vehicle height based on the vehicle height detection signal of the vehicle height detector 157(305).

The vehicle 1 may determine whether the vehicle 1 collides based on the collision detection signal of the collision detector 158, determine that the emergency light turn-on command has been received within a fourth reference time through the input device 120 when it is determined that the vehicle 1 has collided, determine the abnormal state of the driver as an accident state in which consciousness exists when it is determined that the emergency light turn-on command has been received within the fourth reference time through the input device 120, and determine the degree of injury as a minor injury (306).

The vehicle 1 determines whether the seat belt is in a separated state or a coupled state based on the coupling/separation signal of the coupling/separation detector 153 when it is determined that the collision of the vehicle 1 occurs. In this case, the vehicle 1 may determine whether the seat belt is separated within a fifth reference time.

The vehicle 1 may determine whether the door 115 is in an open state based on the door open/close signal of the first open/close detector 151 when it is determined that the seat belt is in the separated state within the fifth reference time in a state in which the collision occurs, check a door opening time when it is determined that the door 115 is in the open state, determine the abnormal state of the driver as the accident state in which consciousness exists when the checked door opening time is shorter than a sixth reference time, and determine the degree of injury as the minor injury (307).

The vehicle 1 may determine whether the door 115 is in the open state based on the door open/close signal of the first open/close detector 151 when it is determined that the seat belt is in the separated state in the state in which the collision occurs, check the door opening time when it is determined that the door 115 is in the open state, determine the abnormal state of the driver as the accident state in which consciousness exists when the checked door opening time is equal to or longer than the sixth reference time, and determine the degree of injury as a minor or severe injury (308).

The vehicle 1 may determine whether the door 115 is in a closed state based on the door open/close signal of the first open/close detector 151 when it is determined that the seat belt is in the separated state within a preset time in the state in which the collision occurs, check a door closing time when it is determined that the door 115 is in the closed state, determine the abnormal state of the driver as the accident state in which consciousness exists and a trapped state when the checked door closing time is equal to or longer than a seventh reference time, and determine the degree of injury as the minor or severe injury (309).

The vehicle 1 may determine whether an emergency light turn-on command is received through the input device 120 when it is determined that the seat belt is in an unseparated state within the fifth reference time in the state in which the collision occurs, determine the abnormal state of the driver as the accident state in which consciousness exists and the trapped state when it is determined that the emergency light turn-on command is received through the input device 120, and determine the degree of injury as the minor or severe injury (309).

The vehicle 1 may determine whether the internal temperature is equal to or higher than the first reference temperature based on the temperature detection signal of the temperature detector 155 when it is determined that the seat belt is in an unseparated state within the fifth reference time in the state in which the collision occurs, determine the abnormal state of the driver as the unconscious state when it is determined that the internal temperature is equal to or higher than the first reference temperature, and determine that the danger factor that puts the occupant in danger is suffocation (310).

The vehicle 1 may determine whether the internal temperature is lower than or equal to the second reference temperature based on the temperature detection signal of the temperature detector 155 when the seat belt is in the unseparated state within the fifth reference time in the state in which the collision occurs, determine the abnormal state of the driver as the unconscious state when it is determined that the internal temperature is lower than or equal to the second reference temperature, and determine that the danger factor that puts the driver in danger is frostbite (311).

The vehicle 1 may determine whether a fuel amount decreases based on the fuel amount detection signal of the fuel amount detector 159 when the seat belt is in the unseparated state within the fifth reference time in the state in which the collision occurs, determine the abnormal state of the driver as the unconscious state when it is determined that the fuel amount decreases, and determine that the danger factor that puts the occupant in danger is a vehicle explosion (312).

The vehicle 1 may include determining whether a fuel change amount decreases over a reference change amount when determining the decrease of the fuel amount.

The vehicle 1 may transmit information on the cause of the abnormal state of the occupant to the external device 2.

The vehicle 1 may transmit rescue information to different external devices in response to whether the occupant is conscious or not and a vehicle state.

When transmitting the rescue information, the vehicle 1 may also transmit information on whether the occupant is conscious, danger factors for the occupant (such as frostbite, burns, suffocation, etc.), and the degree of injury of the occupant.

As illustrated in FIG. 6, when the consciousness of the occupant exists in the state of an accident or breakdown of the vehicle 1, the vehicle 1 may transmit rescue information to a call center such as an insurance company, a tow vehicle support center, and a repair shop, and may transmit the rescue information to a pre-stored emergency contact.

The vehicle 1 may transmit the rescue information to a fire station 119 (or 911), the emergency medical center, a police station, and the pre-stored emergency contact when the consciousness of the occupant does not exist.

The vehicle 1 may transmit the rescue information to a fire station 119 (or 911), the emergency medical center, a police station, the pre-stored emergency contact, and a server of the road traffic authority when it is determined that the vehicle 1 is in a submerged state.

As is apparent from the above, a vehicle according to embodiments of the disclosure can quickly rescue an occupant and increase the probability of rescue by determining whether the occupant is in an abnormal state based on signals detected by a plurality of detectors and transmitting rescue information to an external device when it is determined that the occupant is in the abnormal state.

The vehicle according to embodiments of the disclosure can prevent waste of time and manpower due to rescue and can prevent accidents with other vehicles by determining whether the vehicle is in a normal state based on the detection signals of the plurality of detectors when an emergency light is in a turned-on state, determining a turning-on cause of the emergency light when it is determined that the vehicle is in the normal state, and transmitting guide information about the turning-on cause of the emergency light corresponding to the turning-on cause of the emergency light to the external device.

The vehicle according to embodiments of the disclosure can make situations of an occupant and the vehicle accurately recognized from the outside by transmitting information about a cause of the abnormal state of the occupant and the turning-on cause of the emergency light of the vehicle to the external device.

The vehicle according to embodiments of the disclosure can transmit the rescue information or guide information to the external device suitable for the states of the vehicle and an occupant by determining the abnormal state of the occupant as a suffocation state, an unconscious state, a conscious state, a submerged state, a light injury state, a serious injury state, a trapped state, or an explosive state and transmitting the rescue information in response to the determination result, and by determining the turning-on cause of the emergency light of the vehicle as a collision accident, overturning, parking area search, entry into a parking area, or the temporary parking and transmitting the guide information to the external device in response to the determination result.

The vehicle according to embodiments of the disclosure can prevent an accident by transmitting the turning-on cause of the emergency light of the vehicle in a place where parking is possible such as a parking lot and a rest area as guide information.

As such, the disclosure can improve the quality and merchantability of a vehicle, increase user satisfaction, improve vehicle safety, and secure product competitiveness.

The disclosed embodiments may be implemented in the form of a recording medium storing instructions executable by a computer. The instructions may be stored in the form of program code, and when executed by a processor, a program module may be created to perform the operations of the disclosed embodiments. The recording medium may be implemented as a computer-readable recording medium.

The computer-readable recording medium includes any type of recording medium in which instructions readable by the computer are stored. For example, the recording medium may include a read only memory (ROM), a random access memory (RAM), a magnetic tape, a magnetic disk, a flash memory, an optical data storage device, and the like.

The embodiments disclosed with reference to the accompanying drawings have been described above. It will be understood by those skilled in the art that various changes in form and details may be made therein without departing from the spirit and scope of the disclosure as defined by the appended claims. The disclosed embodiments are illustrative and should not be construed as limiting.

What is claimed is:

1. A vehicle comprising:
   a vehicle body including an exterior and an interior;
   a chassis configured to support the vehicle body;
   a speed detector provided on at least one of the vehicle body or the chassis;
   an emergency light provided on the exterior;
   a plurality of detectors provided on at least one of the exterior or the interior;
   a communication device provided on the vehicle body; and
   a processor configured to determine whether the vehicle is in a normal state based on detection information received from the plurality of detectors when the emergency light is in a turned-on state, determine a turning-on cause of the emergency light based on current location information received by the communication device when it is determined that the vehicle is in the normal state, and control the communication device to transmit guide information corresponding to the determined turning-on cause of the emergency light to an external device, wherein the processor is configured to determine the turning-on cause of the emergency light as temporary parking, and control the communication device to transmit information on the temporary parking to another vehicle when it is determined that a speed detected by the speed detector is slower than or equal to a reference speed.

2. The vehicle according to claim 1, further comprising a camera, wherein the processor is configured to determine whether a current location is a place where parking is possible based on the current location information received by the communication device, recognize a lane based on image information obtained by the camera when it is determined that the current location is a place where parking is possible, and determine the turning-on cause of the emergency light as a search for a parking area or an entry into the parking area based on location information of the recognized lane.

3. The vehicle according to claim 2, wherein the processor is configured to determine whether a vehicle body is located outside or inside the parking area based on the location information of the recognized lane and determine the turning-on cause of the emergency light as a parking area search when it is determined that the speed detected by the speed detector exceeds a reference speed and the vehicle body is located outside the parking area.

4. The vehicle according to claim 3, wherein the processor is configured to determine the turning-on cause of the emergency light as the entry into the parking area when it is determined that the speed detected by the speed detector is slower than or equal to the reference speed and the vehicle body is located inside the parking area.

5. The vehicle according to claim 3, wherein the processor is configured to determine the turning-on cause of the emergency light as temporary parking when it is determined that the speed detected by the speed detector is slower than or equal to the reference speed and the vehicle body is located outside the parking area.

6. The vehicle according to claim 2, wherein the processor is configured to control storage of the image information obtained by the camera when it is determined that the current location is a place where parking is not practical based on the current location information.

7. The vehicle according to claim 1, wherein the processor is configured to determine whether an occupant is in an abnormal state based on the detection information received from the plurality of detectors when the emergency light is in a turned-off state, determine a cause of an abnormality when it is determined that the occupant is in the abnormal state, and control the communication device to transmit rescue information corresponding to the determined cause of the abnormality to the external device.

8. The vehicle according to claim 7, further comprising a storage device configured to store emergency contact information, wherein the processor is configured to control the communication device to transmit the rescue information to the external device based on the emergency contact information stored in the storage device when it is determined that the occupant is in the abnormal state.

9. The vehicle according to claim 8, further comprising an input device, wherein the processor is configured to store in the storage device emergency contact information that is input to the input device.

10. The vehicle according to claim 7, wherein:
the plurality of detectors comprises a first open/close detector configured to output a door open/close signal for opening and closing of a door, a second open/close detector configured to output a window open/close signal for opening and closing of a window, a dust detector configured to output a dust detection signal for fine dust inside the vehicle, and a temperature detector configured to output a temperature detection signal for a temperature inside the vehicle; and
the processor is configured to, when an engine is in a turned-off state by a user, determine the cause of the abnormality of the occupant and whether the occupant is conscious based on the door open/close signal of the first open/close detector, the window open/close signal of the second open/close detector, the dust detection signal of the dust detector, and the temperature detection signal of the temperature detector.

11. The vehicle according to claim 7, further comprising:
an airbag module provided on the vehicle body; and
a wiper provided on the vehicle body;
wherein the plurality of detectors comprises a vehicle height detector configured to output a vehicle height detection signal for a vehicle height and a collision detector configured to output a collision signal for a collision; and
wherein the processor is configured to determine the cause of the abnormality of the occupant as immersion or injury due to an accident in response to reception of a deployment signal of the airbag module and an operation signal of the wiper.

12. The vehicle according to claim 7, wherein:
the plurality of detectors comprises a first open/close detector configured to output a door open/close signal for opening and closing of a door, a collision detector configured to output a collision signal for a collision, a coupling/separation detector configured to output a coupling/separation signal for coupling or separation of a seat belt, a temperature detector configured to output a temperature detection signal for a temperature inside the vehicle, and a fuel amount detector configured to output a fuel amount detection signal for detection of a fuel amount; and
when it is determined that the vehicle is in a collision state based on the collision signal of the collision detector, the processor is configured to determine the cause of the abnormality of the occupant as an injury due to an accident and determine a degree of injury of the occupant and whether the occupant is conscious based on the coupling/separation signal of the coupling/separation detector, the door open/close signal of the first open/close detector, the temperature detection signal of the temperature detector, and the fuel amount detection signal of the fuel amount detector.

13. The vehicle according to claim 1, wherein the processor is configured to determine whether an occupant is in an abnormal state based on the detection information of the plurality of detectors when the emergency light is in a turned-on state, determine a cause of the abnormality when it is determined that the occupant is in the abnormal state, and control the communication device to transmit rescue information corresponding to the determined cause of the abnormality to the external device.

14. A vehicle comprising:
an input device;
an emergency light;
a plurality of detectors;
a communication device; and
a processor configured to determine whether the vehicle is in a normal state based on detection information of the plurality of detectors when the emergency light is in a turned-on state, determine a turning-on cause of the emergency light based on current location information received by the communication device when it is determined that the vehicle is in the normal state, control the communication device to transmit guide information corresponding to the determined turning-on cause of the emergency light to an external device, determine whether an occupant is in an abnormal state based on the detection information of the plurality of detectors when a start-off command is received through the input device, determine a cause of an abnormality when it is determined that the occupant is in the abnormal state, and control the communication device to transmit rescue information corresponding to the determined cause of the abnormality to the external device.

15. The vehicle according to claim 14, further comprising:
a speed detector; and
a camera; and
wherein the processor is configured to determine whether a current location is a place where parking is possible based on the current location information, recognize a lane based on image information obtained by the camera when it is determined that the current location is a place where parking is possible, determine whether a vehicle body is located outside or inside a parking area based on location information of the recognized lane, determine the turning-on cause of the emergency light as a parking area search when it is determined that a speed detected by the speed detector exceeds a reference speed and the vehicle body is located outside the parking area, determine the turning-on cause of the emergency light as an entry into the parking area when it is determined that the speed detected by the speed detector is slower than or equal to the reference speed and the vehicle body is located inside the parking area, and determine the turning-on cause of the emergency light as temporary parking when it is determined that the speed detected by the speed detector is slower than or equal to the reference speed and the vehicle body is located outside the parking area.

16. The vehicle according to claim 15, wherein the processor is configured to control storage of the image information obtained by the camera when it is determined that the current location is a place where parking is not practical based on the current location information.

17. The vehicle according to claim 14, wherein:
the plurality of detectors comprises a first open/close detector configured to output a door open/close signal for opening and closing of a door, a second open/close detector configured to output a window open/close signal for opening and closing of a window, a dust detector configured to output a dust detection signal for fine dust inside the vehicle, and a temperature detector configured to output a temperature detection signal for a temperature inside the vehicle; and
when an engine is in a turned-off state by a user, the processor is configured to determine the cause of the abnormality of the occupant and whether the occupant is conscious based on signals of the first open/close detector, the second open/close detector, the dust detector, and the temperature detector.

18. The vehicle according to claim 15, further comprising:
an airbag module; and
a wiper;
wherein the plurality of detectors comprises a vehicle height detector configured to output a vehicle height detection signal for a vehicle height and a collision detector configured to output a collision signal for a collision; and
the processor is configured to determine the cause of the abnormality of the occupant as immersion or injury due to an accident in response to reception of a deployment signal of the airbag module and an operation signal of the wiper.

19. The vehicle according to claim 14, wherein:
the plurality of detectors comprises a first open/close detector configured to output a door open/close signal for opening and closing of a door, a collision detector configured to output a collision signal for a collision, a coupling/separation detector configured to output a coupling/separation signal for coupling or separation of a seat belt, a temperature detector configured to output a temperature detection signal for a temperature inside the vehicle, and a fuel amount detector configured to output a fuel amount detection signal for detection of a fuel amount; and
when it is determined that the vehicle is in a collision state based on the collision signal of the collision detector, the processor is configured to determine the cause of the abnormality of the occupant as an injury due to an accident and determine a degree of injury of the occupant and whether the occupant is conscious based on the coupling/separation signal of the coupling/separation detector, the door open/close signal of the first open/close detector, the temperature detection signal of the temperature detector, and the fuel amount detection signal of the fuel amount detector.

20. A vehicle comprising:
a vehicle body including an exterior and an interior;
a chassis configured to support the vehicle body;
a speed detector provided on at least one of the vehicle body or the chassis;
an emergency light provided on the exterior;
an airbag module provided on the vehicle body; and
a wiper provided on the vehicle body;
a plurality of detectors provided on at least one of the exterior or the interior, wherein the plurality of detectors comprises a vehicle height detector configured to output a vehicle height detection signal for a vehicle height and a collision detector configured to output a collision signal for a collision;
a communication device provided on the vehicle body; and
a processor configured to determine whether the vehicle is in a normal state based on detection information received from the plurality of detectors when the emergency light is in a turned-on state, determine a turning-on cause of the emergency light based on current location information received by the communication device when it is determined that the vehicle is in the normal state, and control the communication device to transmit guide information corresponding to the determined turning-on cause of the emergency light to an external device, wherein the processor is configured to determine whether an occupant is in an abnormal state based on the detection information received from the plurality of detectors when the emergency light is in a turned-off state, determine a cause of an abnormality when it is determined that the occupant is in the abnormal state, and control the communication device to transmit rescue information corresponding to the determined cause of the abnormality to the external device, and wherein the processor is configured to determine the cause of the abnormality of the occupant as immersion or injury due to an accident in response to reception of a deployment signal of the airbag module and an operation signal of the wiper.

* * * * *

UNITED STATES PATENT AND TRADEMARK OFFICE
CERTIFICATE OF CORRECTION

| | | |
|---|---|---|
| PATENT NO. | : 12,134,345 B2 | Page 1 of 1 |
| APPLICATION NO. | : 17/958919 | |
| DATED | : November 5, 2024 | |
| INVENTOR(S) | : Kyu Hyung Lim | |

It is certified that error appears in the above-identified patent and that said Letters Patent is hereby corrected as shown below:

In the Claims

In Column 25, in Claim 18, Line 1, delete "claim 15," and insert -- claim 14, --.

Signed and Sealed this
Thirty-first Day of December, 2024

Derrick Brent
*Acting Director of the United States Patent and Trademark Office*